United States Patent [19]
Curran et al.

[11] 3,991,065
[45] Nov. 9, 1976

[54] TETRAHYDROQUINOLINE DERIVATIVES

[75] Inventors: Adrian Charles Ward Curran, Newcastle-upon-Tyne; Roger Crossley, Reading; David George Hill, Cookham, all of England

[73] Assignee: John Wyeth & Brother Limited, Maidenhead, England

[22] Filed: Feb. 28, 1975

[21] Appl. No.: 554,259

[52] U.S. Cl. .................. 260/288 R; 260/283 R; 60/287 T; 260/283 S; 260/286 R; 260/289 H; 260/289 R; 424/258
[51] Int. Cl.[2] .................................. C07D 215/40
[58] Field of Search ......... 260/283 S, 287 T, 288 R

[56] References Cited
OTHER PUBLICATIONS
Hagelloch, et al., Zeit. Naturforsch., vol. 6B, p. 147–155 (1951).

Primary Examiner—Nicholas S. Rizzo
Assistant Examiner—Mary Vaughn

[57] ABSTRACT

The invention provides 5,6,7,8-tetrahydroquinoline derivatives which are substituted at the 8-position by an amino group or the group NHCSNHR[5] where R[5] is hydrogen, alkyl of 1 – 3 carbon atoms which may be substituted by dialkylamino; lower alkanoyl or aroyl. The 8-amino cmpounds and those where R[5] is lower alkanoyl or aroyl are intermediates. The other compounds are anti-ulcer agents.

5 Claims, No Drawings

TETRAHYDROQUINOLINE DERIVATIVES

The invention relates to novel tetrahydroquinoline derivatives, to processes for preparing them and to pharmaceutical compositions containing the novel derivatives.

The invention provides a compound of formula I

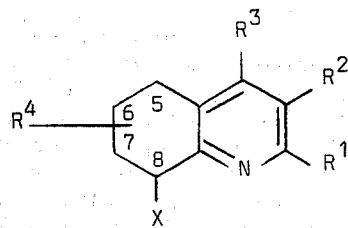

(I)

and pharmaceutically acceptable acid addition salts thereof, wherein $R^1$, $R^2$ and $R^3$ are the same or different and represent hydrogen, or a lower alkyl, phenyl lower alkyl or phenyl radical, any of which radicals may be substituted by lower alkyl, lower alkoxy, nitro or trifluoromethyl, $R^4$ represents hydrogen or single or multiple substitution at the 5, 6 or 7-position by lower alkyl, phenyl lower alkyl or phenyl radicals any of which radicals may be substituted by lower alkyl, lower alkoxy, nitro or trifluoromethyl, X is amino, or $NHCSNHR^5$ where $R^5$ is hydrogen, alkyl of 1-3 carbon atoms, which may be substituted by dialkylamino; lower alkanoyl or aroyl.

When any of $R^1$, $R^2$, $R^3$ or $R^4$ is a lower alkyl radical it has from 1 to 6 carbon atoms and may have a straight or branched chain, e.g. methyl, ethyl, n-, and iso-propyl and n-, s- and t-butyl, $R^4$ may be a gem-dimethyl group. When any of $R^1$, $R^2$, $R^3$ or $R^4$ is a phenyl lower alkyl radical the lower alkyl portion has from 1 to 6 carbon atoms and may be derived from any of the lower alkyl radicals discussed above.

When any of $R^1$, $R^2$, $R^3$ or $R^4$ is a phenyl radical, this may be substituted by lower alkyl, lower alkoxy, nitro or trifluoromethyl.

The term "lower alkoxy" denotes alkoxy radicals having from 1 to 6 carbon atoms e.g. methoxy, ethoxy, propoxy, butoxy, pentoxy or hexyloxy.

Particularly preferred compounds are those in which at least one or more of $R^1$, $R^2$, $R^3$ and $R^4$ is methyl and the others are hydrogen.

Compounds of formula I wherein X is amino or $NHCSNHR^5$, wherein $R^5$ is hydrogen, or alkyl of 1 - 3 carbon atoms which may be substituted by dialkylamino, are anti-ulcer agents which possess one or more of the following pharmacological activities namely anti-ulcer, anti-secretory or gastric anti-histamine activity. The other compounds are intermediates which may be used in the preparation of the active compounds. $R^5$ may be methyl, ethyl or n-propyl.

The compounds of formula I and II can form acid addition salts with inorganic acids e.g. hydrochloric, hydrobromic, sulphuric or nitric acids, or organic acids, e.g. citric, fumaric, maleic or tartaric acids. These acid addition salts are included in the invention.

In the compounds of formula I the carbon atom to which X is attached is asymmetric. Consequently, the compounds can exist in optically active $d$ and $l$ forms. These optically active forms and the racemates are included in the invention. The optically active forms may be separated by standard techniques.

The invention also provides processes for preparing the compounds of formula I.

The preferred process for preparing compounds of formula I wherein X is $NHCSNHR^5$ and $R^5$ is alkyl of 1 - 3 carbon atoms which may be substituted by dialkylamino; or aroyl or alkanoyl comprises reacting a compound of formula I wherein X is amino with an isothiocyantate of formula $R^5$ NCS wherein $R^5$ is as just defined.

The products wherein $R^5$ is aroyl or alkanoyl are useful intermediates for preparing corresponding compounds wherein $R^5$ is hydrogen. Thus a process for preparing compounds of formula I wherein X is $NHCSNH_2$ comprises hydrolysing a corresponding compound of formula I wherein X is NHCSNH Acyl.

The aroyl radical which corresponds to $R^5$ when acyl may be a benzoyl or substituted benzoyl radical e.g. halobenzoyl, such as chlorobenzoyl. When $R^5$ is lower alkanoyl it may have from 2 to 7 carbon atoms examples being acetyl, propionyl, butryl, and hexanoyl.

The hydrolysis of a compound where $R^5$ is aroyl or lower alkanoyl may be carried out by treatment with a suitable base e.g. an alkali or alkaline earth metal hydroxide. Conveniently, sodium or potassium hydroxide may be used.

The start compounds of formula I wherein X is amino are also included in the invention. They may be prepared by treatment of corresponding compounds of formula I wherein X is chloro or bromo with ammonia in a lower alkanol, e.g. methanol or ethanol.

This method is also included in the invention. The compounds of formula I wherein X is chloro or bromo are either known compounds or if novel may be prepared by methods analogous to the preparation of known compounds e.g. by treatment of a corresponding compound of formula I wherein X is hydroxy with thionyl chloride or phosphorus trichloride or trimbromide, or by treatment of an N-oxide of a compound of formula I wherein X is hydrogen with an alkyl sulphonyl halide e.g. Me $SO_2Cl$.

The starting materials wherein X is hydroxy are either known compounds or if novel may be prepared by methods known for analogous compounds e.g. by formation of the N-oxide of a compound of formula I, wherein X is hydrogen with hydrogen peroxide followed by acylation of the N-oxide and hydrolysis to give the compound of formula I wherein X is hydroxy.

A further method for preparing the compounds of formula I wherein X is amino comprises reducing a corresponding oxime of formula I, wherein X is = NOH. The oximes may be prepared by treatment of a corresponding compound of formula I, wherein X is oxo with hydroxylamine or by treatment of a corresponding compound of formula I wherein X is hydrogen with isoamyl nitrite in the presence of butyl lithium.

A further method for preparing compounds of formula I wherein X is $NHCSNHR^5$ and $R^5$ is alkyl of 1–3 carbon atoms which may be substituted by dialkylamino, comprises treating a compound of formula I wherein X is NCS with an amine of formula $R^5NH_2$ wherein $R^5$ is as just defined.

An alternative method for preparing compounds of formula I wherein $R^5$ is hydrogen comprises reacting a compound of formula I wherein X is $NH_2$ with a compound of formula $R_xSi(NCS)_{4-x}$ wherein R is an alkyl, aryl or aralkyl radical or any mixture of these and x is 0, 1, 2 or 3 and then subjecting the product to hydrolysis or alcoholysis. Examples of the compound $R_xSi(NCS)_{4-x}$ are and $x = 3 : R_3SINCS$ $x=0 : Si(NCS)_4$; $x = 1 : RSi(NCS)_3$; $x = 2: R_2 Si(NCS)_2$; wherein R has any of the meanings given above.

When x is 3 the radical $R_x$ may be a tri-alkyl, tri-aryl or tri-aralkyl and is preferably a tri-loweralkyl e.g. tri-methyl.

The reaction with the compound of formula $R_xSI(NCS)_{4-x}$ is conducted under anhydrous conditions, preferably in an inert solvent, for example a hydrocarbon solvent such as benzene, toluene or hexane. Ethers including cyclic ethers such as tetrahydrofuran should be avoided. The product of the first stage of the reaction is a compound of formula I wherein $R^5$ is $SiR_x(NCS)_{3-x}$.

These intermediate compounds are not usually isolated.

The desired compound of formula I wherein $R^5$ is hydrogen is conveniently formed by treating the above intermediate with water or a lower alkanol e.g. ethanol.

The compounds of formula I, wherein X is amino or $NHCSNHR^5$ wherein $R^5$ is hydrogen, or alkyl of 1-3 carbon atoms which may be substituted by dialkyl-amino, are anti-ulcer agents which display one or more of the following activities anti-ulcer, anti-secretory or gastric anti-histamine activity. Anti-ulcer activity is determined by the method of Brodie and Hanson, J. Applied Physiology, 15, 291, 1960.

Anti-secretory activity and Gastric anti-histamine activity are determined by the method of H. Shay, D. Sun and H. Greenstein, Gastroenterology 1954, 26, 906–13.

The invention includes a pharmaceutical composition comprising an active compound of formula I (as defined immediately above) including non-toxic salts thereof, and a pharmaceutically acceptable carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solublisers, suspending agents, binders or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, actose, pectin, dextrin, starch, gelatin, tragacanth, methyl cellulose, sodium carboxymethyl cellulose, a low melting wax and cocoa butter.

The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspension, emulsions, syrups and elixires. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be capsule, cachet or tablet itself, or it can be the appropriate number of any of these in packaged form.

The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminum glycinate, calcium carbonate, magnesium trisilicate, sodium bicarbonate or the alumina gel described in British Specification No. 1,284,394.

The invention is illustrated by the following Examples. Temperatures are in °C.

EXAMPLE 1

8-Hydroxy-3-methyl-5,6,7,8-tetrahydroquinoline

3-Methyl-5,6,7,8-tetrahydroquinoline (50 g.) dissolved in glacial acetic acid (180 ml.) and the solution treated with 30% hydrogen peroxide (70 ml.) and heated at 80° C for 20 hours. The solvent was removed in vacuo and the residual oil diluted with water (25 ml.) and re-evaporated. The resulting oil was dissolved in chloroform (100 ml.), washed with aqueous sodium carbonate (2 × 25 ml.), saturated brine (2 × 25 ml.), dried ($MgSO_4$) and the solvent removed in vacuo to give 3-Methyl-5,6,7,8-tetrahydroquinoline -1-oxide (60 g.) as a pale yellow solid which was used without purification. The N-oxide (60 g.) was dissolved in acetic anhydride (120 ml.) and added to boiling acetic anhydride (120 ml.) and the mixture heated at reflux for 30 minutes. The solvent was removed in vacuo and the residual oil was treated with 10% hydrochloric acid (700 ml.) and the solution heated on a steam bath for 2 hours. The cooled reaction mixture was adjusted to pH 9.0 with sodium hydroxide and extracted with ether (3 × 100 ml.). The combined etheral extracts were washed with saturated brine, dried ($M_gSO_4$) and the solvent removed in vacuo. The resultant oil was distilled at 0.15 mmHg to give a colourless oil (22 g.) b.p. 70-78° C which crystallised from n-hexane to give 8-hydroxy-3-methyl-5,6,7,8-tetrahydroquinoline as colourless needles m.p. 58° C. (Found: C,73.7; H,8.2;N,8.3. $C_{10}H_{13}NO$ requires: C,73.6; H,8.0; N,8.6%).

EXAMPLE 2

8-Chloro-3-methyl-5,6,7,8-tetrahydroquinoline

The 8-hydroxy product of Example 1 (15 g.) was added portionwise to thionyl chloride (33 g.) at 0° C and the mixture stirred at 0° C for 1 hour and heated at reflux for an additional 2 hours. The solvent was removed in vacuo and the residual oil heated at reflux for 1 hour with ethanol (15 ml.) to remove excess thionyl chloride. The resultant precipitate was recrystallised from ethanol-ether to give 8-chloro-3-methyl-5,6,7,8-tetrahydroquinoline hydrochloride as colourless needles (17.4 g.) m p. 177° C. (Found: C, 55.3; H, 6.1; N, 6.5 $C_{10}H_{12}ClN.HCl$ requires: C,55.1; H,6.0; N, 6.4%).

EXAMPLE 3

8-Amino-3-methyl-5,6,7,8-tetrahydroquinoline

The 8-chloro product of Example 2 (17 g.) was dissolved in methanol saturated with ammonia (400 ml.) and heated at 80° in a stainless steel bomb for 24 hours. The solvent was removed in vacuo and the residual oil triturated with anhydrous ether (3 × 50 ml.) and the triturates discarded. The oily solid was dissolved in water and the pH adjusted to 9.0 with sodium carbonate and extracted with ether (3 × 150 ml.). The combined extracts were dried ($MgSO_4$) and the solvent removed in vacuo to give a pale yellow oil (5.5 g.). A sample (500 mg.) was dissolved in anhydrous ether (25 ml.) and the solution treated with excess ethereal hydrogen chloride and the resultant solid recrystallised from methanol-ether to give 8-amino-3-methyl-5,6,7,8-tetrahydroquinoline dihydrochloride quarter hydrate as colourless needles m.p. 210° C. (Found: C,50.5;H,6.9; N,11.6. $C_{10}H_{14}N_2.2HCl$. $1/4H_2O$ requires: C,50.2; H,7.1; N, 11.7%).

EXAMPLE 4

8-Methylthiocarbamoylamino-3-methyl-5,6,7,8-tetrahydroquinoline.

The 8-amino product of Example 3 (free base) (3 g.) was dissolved in acetonitrile (30 ml.) and the solution treated with methylisothiocynate (1.35 g.) and heated at reflux for 2 hours. The solvent was removed in Vacuo and the residual solid recrystallised from absolute ethanol to give the title compound as colourless needles (3 g.) m.p. 113° C. (Found: C,61.4; H,7.3; N, 17.8. $C_{12}H_{17}N_3S$ requires : C, 61.2; H, 7.3; N, 17.9L%). The product displayed anti-ulcer, antisecretory and Gastric anti-histamine activity.

EXAMPLE 5

8-Benzoylthiocarbamoylamino-3-methyl-5,6,7,8-tetrahydroquinoline

A solution of 8-amino-3-methyl-5,6,7,8-tetrahydroquinoline (6. g.) in acetone (48 ml.) was treated with benzoylisothiocyanate (6 g.) and the mixture heated at reflux for 45 minutes. The solvent was removed in vacuo and the residual solid recrystallised from ethanol-ether to give the title compound as colourless needles (7.2 g.) m.p. 168° C. (Found; C,66.5; H, 6.1; N, 13.0 $C_{18}H_{19}N_3OS$ requires: C, 66.4; H, 5.9; N, 12.9%).

EXAMPLE 6

8-Thiocarbamoylamino-3-methyl-5,6,7,8-tetrahydroquinoline

8-Benzoylthiocarbamoylamino-3-methyl-5,6,7,8-tetrahydroquinoline (6 g.) was treated with a 10% sodium hydroxide solution (24 ml.) and the mixture heated on a steam bath for 15 minutes. The cooled reaction mixture was adjusted to pH 1.0 with conc. HCl, filtered to remove benzoic acid and the filtrate adjusted to pH 10.0 with aqueous ammonia. The resultant solid was recrystallised from ethanol to give the hydrate of the title compound as colourless needles (4 g.). m.p. 114° C. (Found C, 55.3; H, 7.3; N, 17.2. $C_{11}H_{15}N_3S.H_2O$ requires: C,55.1; H, 7.3; N, 17.4%). The product displayed anti-ulcer activity.

EXAMPLE 7

8Chloro-3-methyl-5,6,7,8-tetrahydroquinoline

Methanesulphonyl chloride (1.62 ml., 0.02 mol.) was added dropwise at 0° C to 3-methyl-5,6,7,8-tetrahydroquinoline-1-oxide (1.63 g., 0.02 mol.) and the mixture stirred at 0° C for 2 hours and at 80° C for 2.5 hours. The cooled reaction mixture was diluted with water (5 ml.) and the pH adjusted to 9.0 with sodium carbonate and the solution extracted with ethyl acetate (3 × 25 ml.).

The combined extracts were dried ($MgSO_4$) and the solvent removed in vacuo to give a yellow oil (1.2 g.). A sample (500 mgs.) was dissolved in anhydrous ether and treated with excess ethereal hydrogen chloride and the resultant solid recrystallised from ethanol-ether to give the title compound as colourless needles m.p. 177° C identical to authentic material.

EXAMPLE 8

3-Methyl-8-oximino-5,6,7,8-tetrahydroquinoline (42.5g) in methylene chloride (2½l) was stirred at room temperature with manganese dioxide (425g) for 16 hours. The manganese dioxide was removed by filtration and washed with methylene chloride. The filtrate was evaporated to dryness under reduced pressure and the residue was distilled to give 5,6-dihydro-3-methyl-7H-quinoline-8-one (30g) b.p. 142-4° C 0.5mm.

The quinolinone (30g), hydroxylamine hydrochloride (14g), sodium hydroxide (9g), ethanol (165ml) and water (65ml) were stirred and refluxed for 2 hours. Water (100ml) was added and the product was allowed to crystallise overnight. The crystals were removed by filtration and washed with water and dried to give 3-methyl-8-oximino-5,6,7,8-tetrahydroquinoline (27.5g) mp 188° C. Found: C,68.5; H,6.9; N,15.4, $C_{10}H_{12}N_2O$ requires C,68.2; H,6.9; N,15.1%.

EXAMPLE 9

8-Amino-3-methyl-5,6,7,8-tetrahydroquinoline

3-Methyl-8-oximino-5,6,7,8-tetrahydroquinoline (27.5g) was dissolved in ethanol (550ml) and 2N sodium hydroxide solution (550ml) was added. The solution was stirred vigorously and nickel aluminum alloy (41.3g) was added portionwise over 30 mins and the mixture was stirred at room temperature for 2 hours. The reaction mixture was filtered through Kieselguhr and the filter cake washed with ethanol and water. The combined filtrate was evaporated to low bulk under reduced pressure and the residue was extracted with chloroform. The chloroform solution was dried (MgSO₄) and evaporated under reduced pressure. The residue was dissolved in ether (500ml) and filtered and ethereal HCl was added to the filtrate till no more precipitate formed. The solid was removed by filtration and recrystallised from methanol/ether to give 8-amino-3-methyl-5,6,7,8-tetrahydroquinoline hydrochloride (26.2g).

EXAMPLE 10

4-Methyl-8-oximino-5,6,7,8-tetrahydroquinoline

Following the procedure of Examples 1 and 8 4-methyl-5,6,7,8-tetrahydroquinoline may be converted to 4-methyl-8-oximino-5,6,7,8-tetrahydroquinoline.

EXAMPLE 11

8-Amino-4-methyl-5,6,7,8-tetrahydroquinoline

Following the procedure of Example 9 4-methyl-8-oximino-5,6,7,8-tetrahydroquinoline may be converted to 8-amino-4-methyl-5,6,7,8-tetrahydroquinoline which may be obtained as the hydrochloride in the manner of Example 9.

EXAMPLE 12

8-Methylthiocarbamoylamino-4-methyl-5,6,7,8-tetrahydroquinoline

The title compound may be obtained from the 8-amino compound of Example 11 by following the procedure of Example 4.

EXAMPLE 13

3,7,7-Trimethyl-8-oximino-5,6,7,8-tetrahydroquinoline 3,7,7-Trimethyl-5,6,7,8-tetrahydroquinoline may be converted to the title compound by following the procedure of Examples 1 and 8.

EXAMPLE 14

8-Amino-3,7,7-trimethyl-5,6,7,8-tetrahydroquinoline

The oxime of Example 13 may be converted to the title compound by the procedure of Example 9.

EXAMPLE 15

8-Methylthiocarbamoylamino-3,7,7-trimethyl-5,6,7,8-tetrahydroquinoline

The title compound may be prepared by treating the amino compound of Example 14 with methylisothiocyanate according to the procedure of Example 4.

EXAMPLE 16

2-Ethyl-8-oximino-5,6,7,8-tetrahydroquinoline

2-Ethyl-5,6,7,8-tetrahydroquinoline may be converted to the title compound by following the procedures of Examples 1 and 8.

EXAMPLE 17

8-Amino-2-ethyl-5,6,7,8-tetrahydroquinoline

The product of Example 16 may be converted to the title compound by following the procedure of Example 9.

EXAMPLE 18

2-Ethyl-8-methylthiocarbamoylamino-5,6,7,8-tetrahydroquinoline

The amino compound of Example 17 may be converted to the title compound by treatment with methylisothiocyanate according to the procedure of Example 4.

EXAMPLE 19

2-n-Butyl-8-oximino-5,6,7,8-tetrahydroquinoline 2-n-Butyl-5,6,7,8-tetrahydroquinoline may be converted to the title compound following the procedures of Examples 1 and 8.

EXAMPLE 20

8-Amino-2-n-butyl-5,6,7,8-tetrahydroquinoline

The 8-oxime of Example 19 may be converted to the 8-amino title compound by the procedure of Example 9.

EXAMPLE 21

2-n-Butyl-8-methylthiocarbamoylamino-5,6,7,8-tetrahydroquinoline

The product of Example 20 may be converted to the title compound by the procedure of Example 4.

EXAMPLE 22

8-Oximino-2-phenyl-5,6,7,8-tetrahydroquinoline

2-Phenyl-5,6,7,8-tetrahydroquinoline may be converted to the title compound following the procedures of Examples 1 and 8.

EXAMPLE 23

8-Amino-2-phenyl-5,6,7,8-tetrahydroquinoline

The 8-oxime product of Example 22 may be converted to the title compound following the procedure of Example 9.

EXAMPLE 24

8-Methylthiocarbamoylamino-2-phenyl-5,6,7,8-tetrahydroquinoline

The 8-amino-compound of Example 23 may be treated with methylisothiocyanate to give the title compound following the procedure of Example 4.

EXAMPLE 25

Following the procedure of Examples 1 and 8 the indicated 5,6,7,8-tetrahydroquinolines may be converted to the corresponding 8 oximes.

| 5,6,7,8-tetrahydroquinoline (THQ) derivative | |
|---|---|
| Starting material | Final Product (THQ) |
| 3,4-dimethyl-THQ | 3,4-dimethyl-8-oximino-THQ |
| 3,5-dimethyl-THQ | 3,5-dimethyl-8-oximino-THQ |
| 3,6-dimethyl-THQ | 3,6-dimethyl-8-oximino-THQ |
| 2,4-dimethyl-THQ | 2,4-dimethyl-8-oximino-THQ |
| 3-n-butyl-THQ | 3-n-butyl-8-oximino-THQ |
| 3-n-pentyl-THQ | 8-oximino-3-n-pentyl-THQ |
| 3,7-dimethyl-THQ | 3,7-dimethyl-8-oximino-THQ |
| 5-n-butyl-3-methyl-THQ | 5-n-butyl-3-methyl-8-oximino-THQ |
| 3-methyl-6-isopropyl-THQ | 3-methyl-8-oximino-6-isopropyl-THQ |
| 4-n-hexyl-THQ | 4-n-hexyl-8-oximino-THQ |
| 5-methyl-THQ | 5-methyl-8-oximino-THQ |
| 6-ethyl-THQ | 6-ethyl-8-oximino-THQ |
| 7-n-propyl-THQ | 8-oximino-7-n-propyl-THQ |

EXAMPLE 26

Following the procedure of Example 9 the indicated 8-oximes may be converted to the indicated 8-amino compounds which in turn may be converted to the indicated 8-methylthiocarbamoylamino-5,6,7,8-tetrahydroquinolines by the procedure of Example 4.

| 5,6,7,8-tetrahydroquinoline (THQ) Derivative | | |
|---|---|---|
| Starting material | 8-amino-THQ | 8-methylthiocarbamoyl-THQ |
| 3,4-dimethyl-8-oximino-THQ | 8-amino-3,4-dimethyl-THQ | 3,4-dimethyl-8-methylthiocarbamoyl-THQ |
| 3,5-dimethyl-8-oximino-THQ | 8-amino-3,5-dimethyl-THQ | 3,5-dimethyl-8-methylthiocarbamoyl-THQ |
| 3,6-dimethyl-8-oximino-THQ | 8-amino-3,6-dimethyl-THQ | 3,6-dimethyl-8-methylthiocarbamoyl-THQ |
| 2,4-dimethyl-8-oximino-THQ | 8-amino-2,4-dimethyl-THQ | 2,4-dimethyl-8-methylthiocarbamoyl-THQ |
| 3-n-butyl-8-oximino-THQ | 8-amino-3-n-butyl-THQ | 3-n-butyl-8-methylthiocarbamoyl-THQ |
| 3-n-pentyl-8-oximino-THQ | 8-amino-3-n-pentyl-THQ | 8-methylthiocarbamoyl-3-n-pentyl-THQ |
| 3,7-dimethyl-8-oximino-THQ | 8-amino-3,7-dimethyl-THQ | 3,7-dimethyl-8-methylthiocarbamoyl-THQ |
| 5-n-butyl-3-methyl-8-oximino-THQ | 8-amino-5-n-butyl-3-methyl-THQ | 5-n-butyl-3-methyl-8-methylthiocarbamoyl-THQ |
| 3-methyl-8-oximino-6-iso-propyl-THQ | 8-amino-3-methyl-6-isopropyl-THQ | 3-methyl-8-methylthiocarbamoyl-6-isopropyl-THQ |
| 4-n-hexyl-8-oximino-THQ | 8-amino-4-n-hexyl-THQ | 4-n-hexyl-8-methylthiocarbamoyl-THQ |
| 5-methyl-8-oximino-THQ | 8-amino-5-methyl-THQ | 5-methyl-8-methylthiocarbamoyl-THQ |
| 6-ethyl-8-oximino-THQ | 8-amino-6-ethyl-THQ | 6-ethyl-8-methylthiocarbamoyl-THQ |
| 8-oximino-7-n-propyl-THQ | 8-amino-7-n-propyl-THQ | 8-methylthiocarbamoyl-7-n-propyl-THQ |

EXAMPLE 27

Following the procedure of Example 5 the following compounds may be prepared from 8-amino-3-methyl-5,6,7,8-tetrahydroquinoline by replacing benzoylisothiocyanate by the indicated isothiocyanate. The 8-acyl-thiocarbamoyl compounds formed may be converted to 8thiocarbamoylamino-3-methyl-5,6,7,8-tetrahydroquinoline by hydrolysis in the manner described in Example 6.

| Isothiocyanate | 8-acyl-thiocarbamoyl-tetrahydroquinoline-(THQ) |
|---|---|
| acetylisothiocyanate | 8-acetylthiocarbamoyl-3-methyl-THQ |
| propionylisothiocyanate | 3-methyl-8-propionylthiocarbamoyl-THQ |
| p-chlorobenzoylisothiocyanate | 8p-chlorobenzoylthiocarbamoyl-3-methyl-THQ |

EXAMPLE 28

8-(2-Diethylaminoethyl)thiocarbamoylamino-3-methyl-5,6,7,8-tetrahydroquinoline 8-amino-3-methyl-5,6,7,8-tetrahydroquinoline may be treated with diethylaminoethyl isothiocyanate according to the procedure of Example 4 to give the title compound.

We claim:
1. A compound of formula I

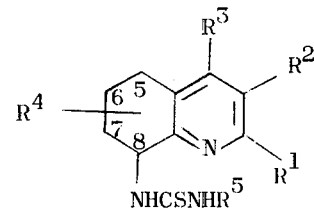

and pharmaceutically acceptable acid addition salts thereof, wherein:

$R^1$, $R^2$ and $R^3$ are independently hydrogen, or alkyl of 1 to 6 carbon atoms;
$R^4$ represents hydrogen or substitution at the 5,6 or 7-position by alkyl of 1 to 6 carbon atoms;
$R^5$ is hydrogen, or alkyl of 1-3 carbon atoms, with the proviso that when any two of $R^1$, $R^2$ and $R^3$ are lower alkyl and are on adjacent carbon atoms then they are selected from normal and secondary alkyl groups.

2. A compound as claimed in claim 1, wherein $R^5$ is methyl.

3. A compound as claimed in claim 1 wherein $R^1$, $R^2$, $R^3$ and $R^4$ are independently hydrogen or methyl.

4. A compound as claimed in claim 1 which is 8-methylthiocarbamoylamino-3-methyl-5,6,7,8-tetrahydroquinoline or a pharmaceutically acceptable acid addition salt thereof.

5. A compound as claimed in claim 1 which is 8-thiocarbamoylamino-3-methyl-5,6,7,8-tetrahydroquinoline or a pharmaceutically acceptable acid addition salt thereof.

* * * * *

UNITED STATES PATENT OFFICE
CERTIFICATE OF CORRECTION

PATENT NO. : 3,991,065
DATED : November 9, 1976
INVENTOR(S) : Adrian Charles Ward Curran, Roger Crossley, David George Hill It is certified that error appears in the above-identified patent and that said Letters Patent are hereby corrected as shown below:

On the Cover Sheet, After [21] Application No.: 554,259 insert -- [30] Foreign Application Priority Data

March 5, 1974 United Kingdom 9763/74

Signed and Sealed this

Eighth Day of February 1977

[SEAL]

Attest:

RUTH C. MASON
*Attesting Officer*

C. MARSHALL DANN
*Commissioner of Patents and Trademarks*